US008187424B2

(12) United States Patent
Haran et al.

(10) Patent No.: US 8,187,424 B2
(45) Date of Patent: May 29, 2012

(54) TIME DOMAIN SPECTROSCOPY (TDS)-BASED METHOD AND SYSTEM FOR OBTAINING COINCIDENT SHEET MATERIAL PARAMETERS

(75) Inventors: Frank M. Haran, North Vancouver (CA); Payam Mousavi, Coquitlam (CA); David Jez, Vancouver (CA); Steven Dodge, Burnaby (CA)

(73) Assignee: Honeywell ASCA Inc., Mississauga, Ontario (CA)

( * ) Notice: Subject to any disclaimer, the term of this patent is extended or adjusted under 35 U.S.C. 154(b) by 714 days.

(21) Appl. No.: 12/184,371

(22) Filed: Aug. 1, 2008

(65) Prior Publication Data
US 2010/0024999 A1 Feb. 4, 2010

(51) Int. Cl.
*D21F 11/00* (2006.01)
(52) U.S. Cl. ........ 162/198; 162/263; 356/316; 356/338; 356/51
(58) Field of Classification Search .................. 162/198, 162/263; 356/51, 316, 394
See application file for complete search history.

(56) References Cited

U.S. PATENT DOCUMENTS

| 7,609,366 B2* | 10/2009 | MacHattie et al. ......... 356/5.05 |
| 2007/0137823 A1 | 6/2007 | Haran |
| 2008/0137068 A1* | 6/2008 | Ouchi et al. ..................... 356/51 |

FOREIGN PATENT DOCUMENTS

| JP | 2002-292832 A | 10/2002 |
| JP | 2007-218662 A | 8/2007 |
| JP | 2008-151591 A | 7/2008 |

* cited by examiner

*Primary Examiner* — Matthew Daniels
*Assistant Examiner* — Jacob Thomas Minskey
(74) *Attorney, Agent, or Firm* — Jetter Associates, P.A.

(57) ABSTRACT

An in-situ time domain spectroscopy (TDS)-based method (200) for non-contact characterization of properties of a sheet material while being produced by a manufacturing system (700). A time domain spectrometry system (100) and calibration data for the system is provided. The calibration data includes data for transmitted power through or reflected power from the sheet material as a function of a moisture content of the sheet material. At least one pulse of THz or near THz radiation from a transmitter (111) is directed at a location on a sheet material sample (130) while being processed by the manufacturing system (700). Transmitted or reflected radiation associated with at least one transmitted or reflected pulse from the sample location is synchronously detected by a detector (110) to obtain the sample data. The sample data, which is coincident data, is processed together with the calibration data (207, 208, 209) to determine at least one, and generally a plurality of properties of the sheet material sample (130) selected from caliper, basis weight and moisture content.

10 Claims, 6 Drawing Sheets

TIME DOMAIN SPECTROSCOPY (TDS)-BASED METHOD AND SYSTEM FOR OBTAINING COINCIDENT SHEET MATERIAL PARAMETERS

FIELD OF THE INVENTION

The invention generally relates to process measurement systems, and more specifically to time domain spectroscopy (TDS)-based measurement systems for measuring one or more parameters of manufactured sheet materials, such as paper or plastics.

BACKGROUND

On-line measurements made during the paper-making process generally include caliper (thickness), basis weight and moisture (e.g. % moisture). The measurements can be used for controlling process variables with the goal of maintaining output quality and thus minimizing the quantity of rejected product. The measurements are generally obtained at multiple locations across the paper sheet by scanning the sensor(s) in what is known as the cross direction (CD), or the measurements can be made at multiple locations down the length of the paper machine in what is known as the machine direction (MD). As described below, the measurements of caliper, basis weight and moisture content are conventionally made using three separate sensors/gauges.

Caliper measurements are generally either made by a device that physically contacts the sheet material or by non-physically contacting laser triangulation based device. Caliper sensors require access to both sides of the sheet. The contacting device is generally disliked because it can suffer from wear or build up issues, and can mark the sheet. The laser based device generally has a high degree of alignment tolerance requirements.

Basis weight sensors predominately use a nuclear radiation source and therefore are generally accompanied by regulatory issues. Like caliper sensors, basis weight sensors need access to both sides of the sheet.

Moisture measurement systems typically comprise infrared spectroscopy systems to measure the moisture content of the sheet. The spectroscopy system can operate either in transmission or reflection mode.

Requiring separate sensors/gauges for the measurements of caliper, basis weight and moisture has several disadvantages. One disadvantage is system cost and complexity. Another disadvantage is the inability to provide coincident measurements, where "coincident" as used herein refers to a plurality of different measurements made both at the same time and at the same location. When the measurements are not all made on the same paper location, errors can occur when using the respective measurements in combination to infer other information about the paper. For example paper on the scale of millimeters to centimeters can have relatively high variations in certain parameters due to the formation process. In the case of formation induced moisture variation, The moisture level of two adjacent spots on a paper sheet separated by 1 cm is known to be as high as 1%. When combining two measurements to calculate a third parameters such as basis weight and percent moisture to calculate the dry weight, If the two measurements are not made at the same location on the paper then an error in the dry weight calculated can result due to significant differences in moisture content at the respective measurement locations.

SUMMARY

The Summary is provided to comply with 37 C.F.R. §1.73, presenting a summary of the invention briefly indicating the nature and substance of the invention. It is submitted with the understanding that it will not be used to interpret or limit the scope or meaning of the claims.

Embodiments of the present invention describe in-situ time domain spectroscopy (TDS)-based methods and systems therefrom for characterizing one or more properties of a sheet material (e.g. paper or plastic) produced by a manufacturing system. Systems and methods according to embodiments of the invention thus are operable in a non-contact mode.

The method comprises providing a time domain spectrometry (TDS) system and calibration data for the system, the calibration data comprising transmitted power or field through or reflected power or field from the sheet material as a function of a moisture content of the sheet material, as well as generally a grade dependent calibration for the dry contents' refractive index and density.

At least one pulse of terahertz (THz) or near THz radiation is directed at a sample location on a sheet material sample while being processed by the manufacturing system.

As used herein, radiation having a frequency of between 0.05 THz and 50 THz is referred to herein as being "THz or near THz radiation". In the case of THz radiation, the technique comprises THz-TDS. Although the boundaries of the THz region are not exactly defined, the boundaries are generally taken to lie between 30 μm and 1500 μm wavelength, or 10 THz and 0.2 THz frequency, or 330 cm$^{-1}$ and 7 cm$^{-1}$ wavenumber.

Transmitted radiation comprising at least one transmitted pulse or reflected radiation comprising at least one reflected pulse from the sample location is synchronously detected. Data from the transmitted or reflected pulse together with the calibration data are processed to determine at least one property, and generally a plurality of properties, of the sheet material sample selected from the moisture content, physical thickness (caliper) and basis weight. As used herein, "moisture content" includes all moisture measures for the sheet material including, but not limited to, water weight (WW) and percent moisture (PM).

As known in the art, TDS is a spectroscopic technique where a generation and detection scheme is used to probe properties of materials with short pulses of electromagnetic radiation. Using THz or near THz radiation, TDS has been found by the present Inventors to be sensitive to detect signals allowing determination of caliper, basis weight and moisture of the sheet-material, based on changes to the amplitude of the radiation and/or the phase of the signal. The amplitude of the signal can be used to obtain information about the water content of the paper or other sheet material samples, while the phase of the signal can be used to obtain the thickness and dry weight volume fraction of the paper or other sheet material sample. This information in combination with calibration data can be used to obtain the moisture content (such as expressed as PM), caliper and basis weight of the sheet material sample (e.g. paper). Given basis weight, the WW can be determined from the PM.

DETAILED DESCRIPTION

Figure 1:
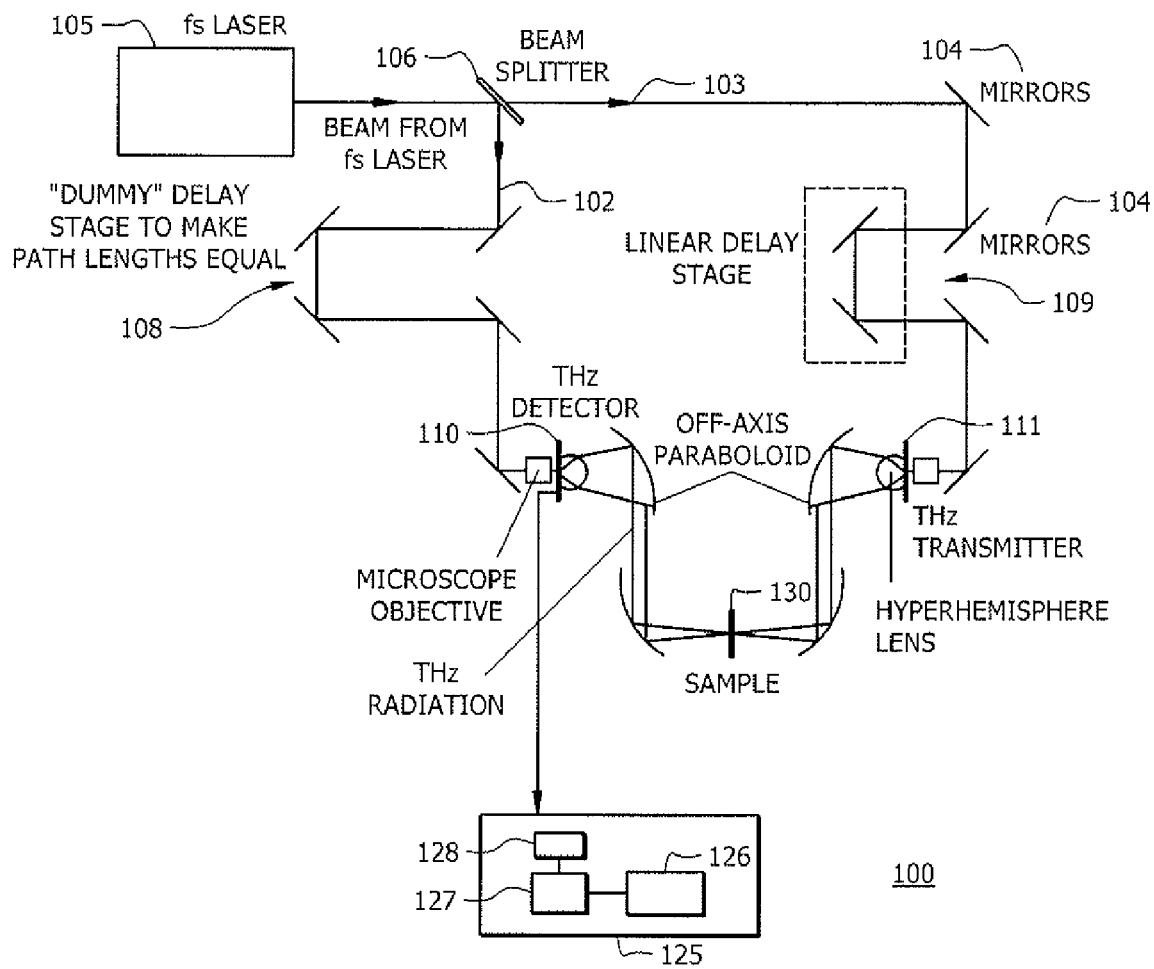
FIG. 1 is a simplified representation of an exemplary THz or near THz-TDS transmission-based sheet measurement system, according to an embodiment of the invention.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention. The invention will now be described more fully hereinafter with reference to accompanying drawings, in which illustrative embodiments of the invention are shown. This invention, may however, be embodied in many different forms and should not be construed as limited to the embodiments set forth herein.

The present Inventors have found that near THz or THz-TDS can be used in-situ to coincidentally obtain one or more parameters/properties of a sheet material including the water weight, physical thickness (caliper) and dry weight volume fraction. The sheet material can comprise paper or a plastic. From these parameters/properties in combination with one or more calibration parameters, caliper, basis weight and moisture content including PM and/or WW of the sheet material may be obtained.

The calibration parameters generally include the known Debye parameters used in a double Debye model which obtains the dielectric constant of water in the THz or near THz spectral region of the electromagnetic spectrum, the dry content refractive index of the paper or other sheet material under test, the density of the dry content of the paper under test, and the coefficients of a fit of water weight to a log of the power ratio of reference signal to that of a transmitted (or reflected) sample signal.

Moisture content (such as expressed as percent moisture (PM)) and WW can be obtained by measuring the near THz or THz power or field transmitted through a sample and comparing it with a reference pulse (without sample) and therefore obtaining by how much the water has attenuated the pulse. As known in the art, PM is related to WW via the relation: PM=WW/BW; where BW represents basis weight (repeated in equation 12 below). BW=WW+DW; where DW represents dry weight (no water present). From this attenuation measurement and calibration data (e.g. from a laboratory calibration), measurements relating to the amount of water present in the sheet material may be determined.

Moisture content (such as expressed as PM or WW) can also be obtained via a similar method in a system having a reflection geometry. In a reflection-based system, the THz transmitter/emitter and THz receiver/detector on the same side of the sample. In such a system, the reference signal is taken from a non-water containing reflective surface and the sample signal is the reflected THz or near THz signal from the sample.

For Transmittance-Based Systems:

The sample caliper and dry weight volume fraction can be obtained by fitting a model for the transmittance function for a single layer film (e.g. sheet of paper) to that of the experimentally obtained transmitted THz pulse. One physical model that can be used is the following: [see Born, M. and Wolf, E, Principles of Optics, $4^{th}$ edition, Pergamon Press (1970)]

$$t = \frac{t_{12} \cdot t_{23} \cdot e^{i\beta}}{1 + r_{12} \cdot r_{23} \cdot e^{2i\beta}} \quad (1)$$

Where $t_{12}$ and $t_{23}$ are the transmission coefficients at the first and second film layer interfaces respectively, $r_{12}$ and $r_{23}$ are the reflection coefficients at the first and second film layer interfaces respectively, and $$\beta = \frac{\omega}{c} \cdot n_p \cdot h.$$

Where $\omega$ is the angular frequency of the THz radiation, c is the speed of light, h is the film thickness and $n_p$ is the complex refractive index of the film (e.g. paper). The transmission and reflection coefficients in equation (1) are given by:

$$t_{12} = \frac{2n_a}{n_a + n_p} \quad (2)$$

$$t_{23} = \frac{2n_p}{n_a + n_p}$$

$$r_{12} = \frac{n_a - n_p}{n_a + n_p}$$

$$r_{23} = \frac{n_p - n_a}{n_a + n_p}$$

Where $n_a$ and $n_p$ are the refractive indices of air and paper (or other sheet material), respectively. The refractive index of air is approximately equal to 1 and the refractive index of paper is a linear combination of the paper's dry content refractive index and the refractive index of water. The dry content refractive index is generally obtained via a calibration step and has been found by the authors to depend upon paper type.

The refractive index of water is obtained via its dielectric function which can generally be accurately described with a double Debye model of the form:

$$\varepsilon_w(\omega) = \varepsilon_\infty + \frac{\varepsilon_s - \varepsilon_2}{1 + i\omega\tau_1} + \frac{\varepsilon_2 - \varepsilon_\infty}{1 + i\omega\tau_2} \quad (3)$$

Where $\in_s$ is the static dielectric constants $\in_\infty$ is the limiting value dielectric constant at high frequency, $\in_2$ is an intermediate value of dielectric constant and the time constant $\tau_1$ and $\tau_2$ are related to the translational and rotational diffusion, hydrogen bond rearrangement and structural rearrangement. Although a double Debye model is generally described herein to describe the water's dielectric constant, other models can also be used, e.g. single Debye model, or certain non-Debye-based models.

The refractive index of the sheet material can be obtained via the dielectric constant of the sheet material (e.g. paper):

$$\in_p(\omega) = f_w \cdot \in_w(\omega) + f_d \cdot \in_d \quad (4)$$

Where $f_w$ and $f_d$ are the volume fractions of water and dry sheet material, such as paper. If the paper only contains water and dry content (e.g. cellulose) then $f_w = 1 - f_d$. It has been found by the present Inventors that $\in_d$ can be approximated as a real constant over the frequency range of interest. However, embodiments of the invention also include the case where the dielectric constant of the film could be absorptive (non-zero imaginary component to dielectric constant) and dispersive.

The refractive index is related to the dielectric function by the following expressions:

$$n_{real} = Re(\sqrt{\in_p})$$

$$n_{img} = Im(\sqrt{\in_p}) \quad (5)$$

In one embodiment, the transmittance of the THz pulse through the paper is modeled using the transmittance function given in equation (1). A two parameter least squares fit of the model to the experimentally obtained transmitted THz pulse can then be performed. The two fitted parameters obtained from the fit are dry content volume fraction and physical thickness. As described above the water content can be obtained from the amplitude of the transmitted pulse.

For Reflection-Based Systems:

The same methodology described above in the case of transmittance system arrangement can be used in a reflection arrangement where instead of the expression for transmission (equation (1)), an expression for the reflectance can be used:

$$r = \frac{r_{12} + r_{23} \cdot e^{2i\beta}}{1 + r_{12} \cdot r_{23} \cdot e^{2i\beta}} \quad (6)$$

FIG. 1 is a simplified representation of an exemplary THz or near THz-TDS transmission-based sheet measurement system 100, according to an embodiment of the invention. A variety of other THz-TDS-based measurement system arrangements may be used with embodiments of the invention, since embodiments of the invention generally involve new uses for THz or near THz-TDS systems supported by new algorithms and related calibration data that permit in-situ coincident measurement of a plurality of properties of the sheet material including the moisture content (such as PM and/or WW), caliper (thickness) and basis weight.

System 100 comprises a near THz or THz generator including at least one pulsed laser source (e.g. femtosecond (fs) laser) 105 for emitting a beam of optical pulses. A beam splitter 106 splits the optical beam into two beams, a reflected beam 102 and a transmitted beam 103. The reflected beam 102 is directed to reflective delay comprising optics 108 including a "dummy" delay stage. The purpose of the dummy delay is to make both the source (transmitter) and receiver (detector) arms of the THz-TDS system 100 have nominally equal optical path length; this results in the source and receiver fs-pulses being derived from the same original fs-pulse. The intention of the dummy delay is to minimize noise. However this dummy delay is not generally required and the THz-TDS system 100 can be also generally operated without it in certain applications.

The transmitted beam 103 is directed via mirrors 104 to delay comprising optics 109 shown as linear delay stage. The delay comprising optics 108 and 109 are configured to make the optical path length of the reflected beam 102 to the detector 110 be nominally equal to the optical path length of the transmitted beam 103 to the near THz or THz transmitter 111.

The near THz or THz transmitter 111 includes a transmit antenna operable for emitting THz or near THz radiation pulses having a frequency between 0.05 THz and 50 THz at a sample location on the sheet material. The THz transmission antenna will generally have a bias voltage applied to it (not shown in FIG. 1) which can be modulated for the utilization of a lockin detection scheme in system 100. The detector 110 includes a receive antenna operable to receive near THz or THz radiation transmitted by the location on the sample 130 that is irradiated by the incident radiation. Embodiments of the invention are not limited to using photoconductive antennae as described herein. For example, other methods such as optical rectification using crystals such as Zinc Telluride (ZnTe) may also be used. The THz detector 110 is coupled to the receive antenna and is also coupled to receive the delayed optical pulses optical from delay comprising optics 108 for synchronously detecting the THz or near THz radiation transmitted by the sheet material sample 130. The detector 110 generates electrical detection signals. Although FIG. 1 shows a THz focused beam interacting with the sample 130, it is understood by those having ordinary skill in the art that other optical geometries such as a collimated geometry can also be used.

A signal processing system 125 is coupled to the detector 110 to receive the electrical detection signals. The signal processing system 125 comprises a memory 126 for storing calibration data that is generally in the form of calibration coefficients that permit calculation of the moisture content, caliper or basis weight of the sheet material. Memory 126 can also include a stored estimate for the refractive index for a dry sample of the sheet material and the density of the sheets dry content. Signal processing system 125 also includes processing electronics 128 which generally includes a transimpedance (current to voltage)-amplifier, filter and analog to digital (A/D) converter. A processor (e.g. DSP) 127 receives processed electrical signal (amplified, filtered and converted to a digital signal) from processing electronics 128. The processor 127 combines a signal associated with the transmitted pulse together with the calibration data and a reference signal pulse to determine at least one property of the sheet material sample selected from the moisture content, basis weight and caliper.

The detection electronics generally utilizes a lockin detection scheme (not shown in FIG. 1) in which a modulated bias voltage is applied to the transmit antenna. This modulation signal is also fed to lockin detection electronics which increases the signal-to-noise ratio of the system as well as minimizes the effect of any background signal. A mechanical chopper is can be used in the source femtosecond laser beam 105 to realize the lockin detection—in the case a DC bias voltage is applied to the antenna.

Figure 2:
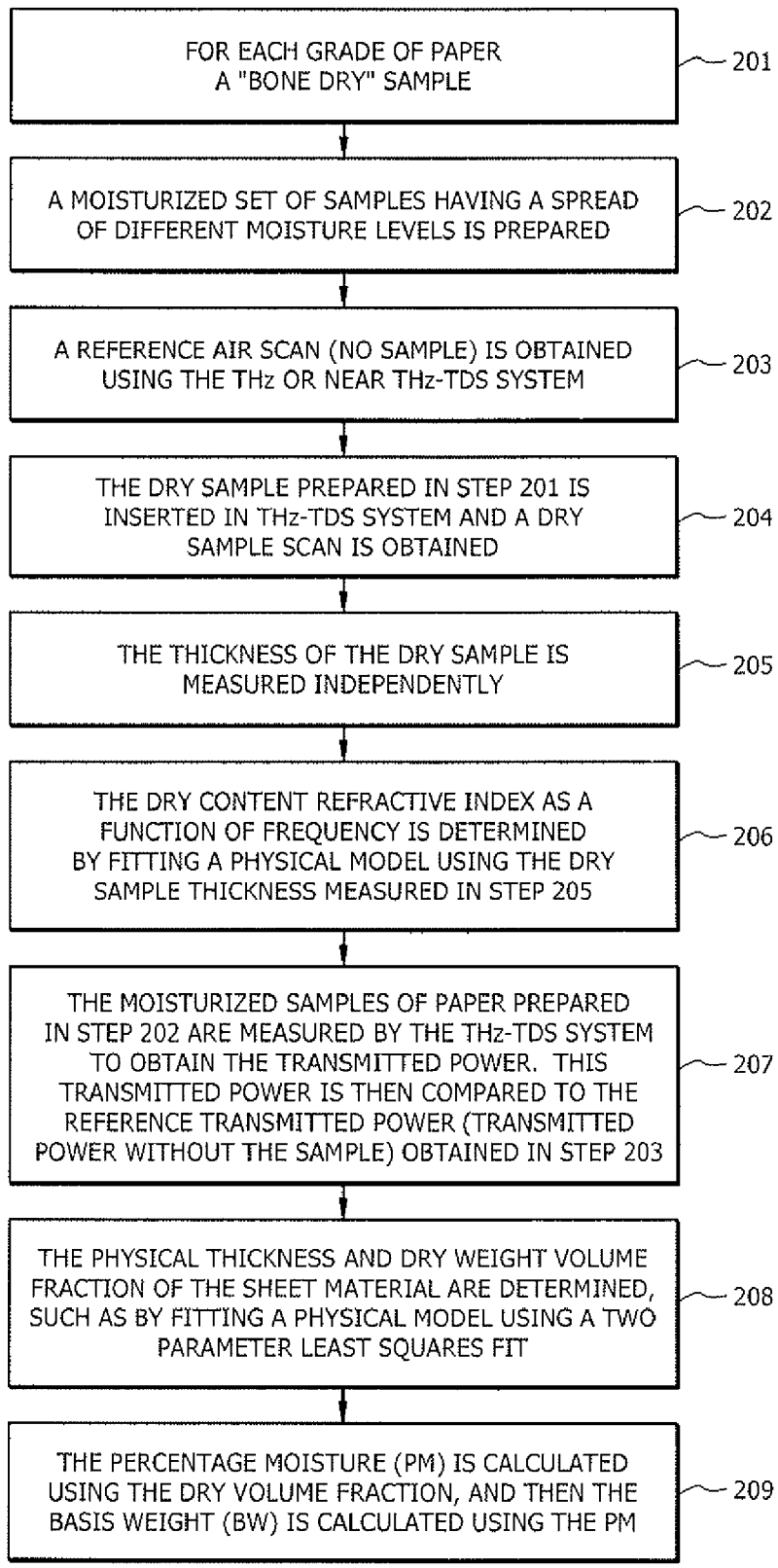
FIG. 2 shows steps in an exemplary method for obtaining caliper (thickness), basis weight and percent moisture for a sheet material sample described as being paper, from a THz or near THz-TDS system, such as the transmission system shown in FIG. 1.

An exemplary method 200 is described below for coincidentally obtaining caliper (thickness), basis weight and percent moisture for a sheet material sample described as being paper, from a THz or near THz-TDS system, such as system 100. Referring, to FIG. 2, in step 201, for each grade of paper a "bone dry" sample (essentially moisture free, hereafter a "dry sample") is made following standard procedures known in the art. In step 202, for each grade of paper, a moisturized set of samples having a spread of different known moisture levels is prepared. These samples should cover the moisture range over which the system generally operates. Step 203 comprises a reference air scan (i.e. a scan with no sample present) using the THz or near THz TDS system. In step 204 the dry sample prepared in step 201 is inserted in THz-TDS system and a dry sample scan is obtained. In step 205 the thickness of the dry sample is measured independently. One method for measuring the thickness of the dry sample is a lab TAPPI gauge.

In step 206 the dry content refractive index as a function of frequency is determined by fitting a physical model using the dry sample thickness measured in step 205. The dry content refractive index of the sample can then be calculated by fitting the model for the transmittance function for a transmittance-based system (equation (1)) or the reflectance function for a reflection-based system (equation (6)). When the fit is performed the thickness measurement from step 205 (e.g. from the TAPPI caliper gauge) is input and it is generally assumed that the contribution of water to the refractive index of the sample is negligible, i.e. we the dry content fraction to 1. From this fit the dry content refractive index is obtained which generally constitutes one of the calibration parameters. The present Inventors have found that for paper this dry content refractive index parameter typical lies between 1.3 and 1.5 in the THz region.

The physical model for step 206 can comprise modeling the sheet material (e.g. paper) as a thin dielectric slab comprising a homogeneous mixture of air, dry content (cellulose and ash), and water. In the model, the proportions of the mixture and the thickness of the sheet material can be varied. Existing data for the dielectric constant of water in the THz regime at different temperatures can be obtained. A double Debye model can be used to model the electromagnetic response of the water at the near THz or THz frequency.

For example, the model fitting for step 206 can comprise performing an least squares fit. It can be assumed that the sample consists entirely of the dry sample (i.e. 0% moisture).

Figure 3:
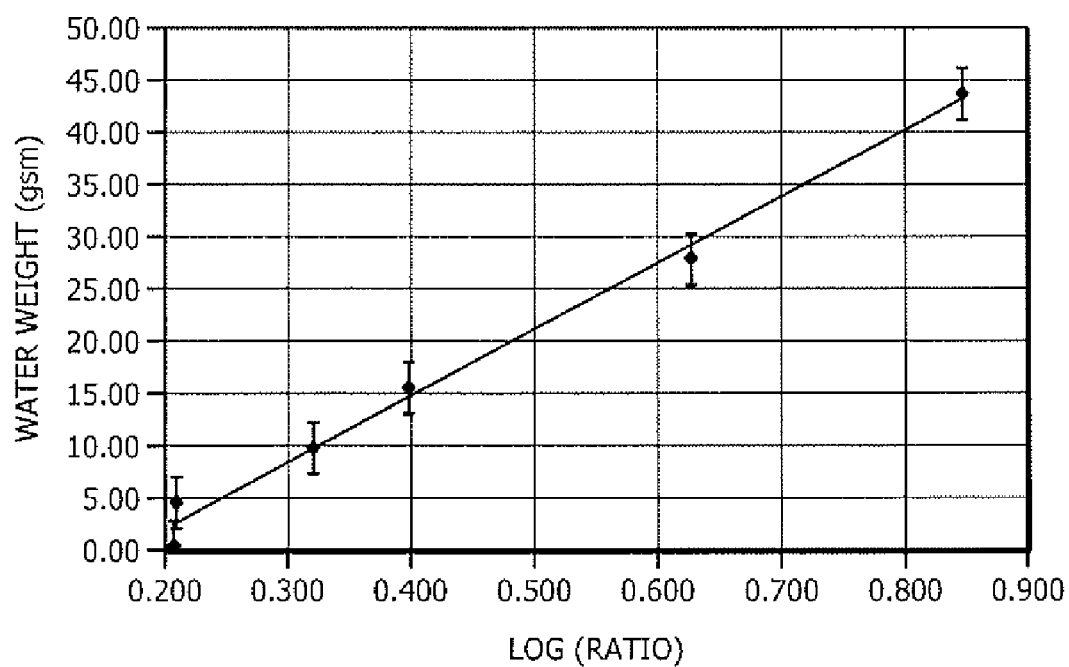
FIG. 3 is a calibration curve that relates the water weight (WW) to the log of the ratio the integrated power spectral density of a reference transmitted pulse and a measured transmitted pulse, according to an embodiment of the invention.

Step 207 comprises measuring the moisturized samples of paper prepared in step 202 using the THz-TDS system to obtain the transmitted power or the transmitted field in the case of a transmission-based system, or reflected power or reflected field in the case of a reflectance-based system. In the case of a transmission-based system, the transmitted power or transmitted field is then compared to the reference transmitted power (transmitted power without the sample) obtained in step 203. The calibration curve for WW can be displayed as shown in FIG. 3. The following function is plotted in FIG. 3:

$$WW(y_i(t), y_o(t)) = m \times \log_e\left(\frac{PSD(y_i(t))}{PSD(y_o(t))}\right) + C \quad (8)$$

Where WW is the water weight in grams per square meter (GSM), $y_i(t)$ is the reference or incident pulse (no sample present), $y_o(t)$ is the output or sample pulse (sample present) and m and C are calibration constants. PSD stands for the integrated power spectral density and is defined as the integral over frequency of the norm-squared Fourier transform. WW shown in FIG. 3 plotted against the log of the ratio of the reference and sample pulse power can be seen to be essentially linear, although there is no requirement for a linear function.

Figure 4:
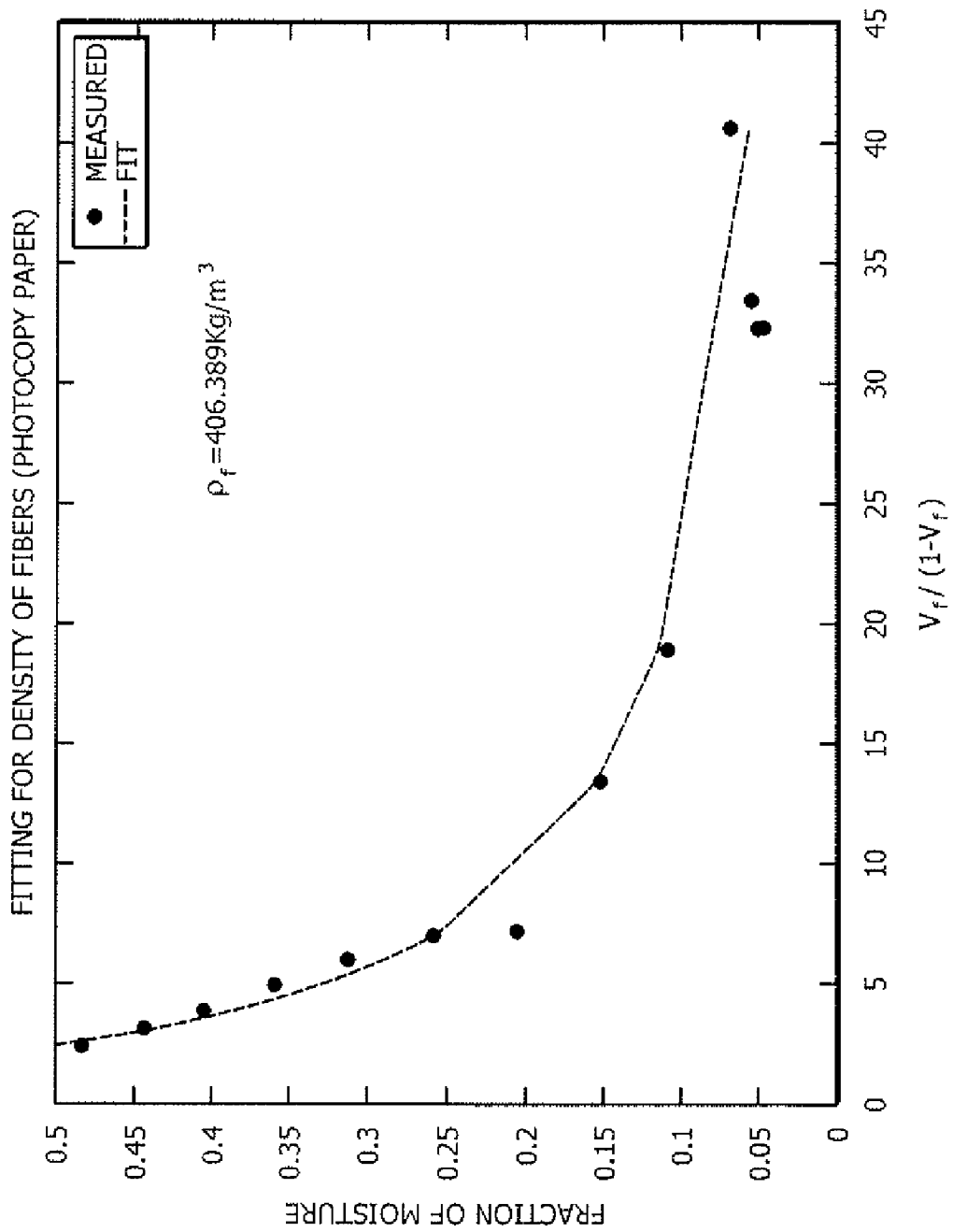
FIG. 4 shows a calibration curve fit based on measured values for the fraction of moisture obtained from photocopy paper.

The same data set obtained from the moisturized sample set in step 202 can be used to obtain another calibration parameter, density of dry content, $\rho_f$. This calibration parameter can be obtain by constructing a plot of fractional moisture content versus $(v_f/(1-v_f))$ and fitting the expression given in equation (9) to obtain $\rho_f$. This fit is shown in FIG. 4, which shows a calibration curve fit based on measured values faction of moisture values obtained from a sample comprising photocopy paper. The abscissa in this figure is $v_f/(1-v_f)$ where $v_f$ is the dry weight volume fraction obtained from the fit of the physical to the transmitted THz pulse. The ordinate in FIG. 4 is the fractional water content for the sample under test. This fractional water content can be obtained using an independently measurement technique and typically be obtained gravimetrically in a laboratory. The density of dry paper content can be obtained by a least squares parameter fit to the model:

$$PM = \frac{\rho_f}{\rho_w}\left(\frac{1}{v_f} - 1\right) \quad (9)$$

Where PM is the percent moisture and $\rho_w$ and $\rho_f$ are the densities of water and dry paper content. The density of water can be obtained from open literature.

Figure 5:
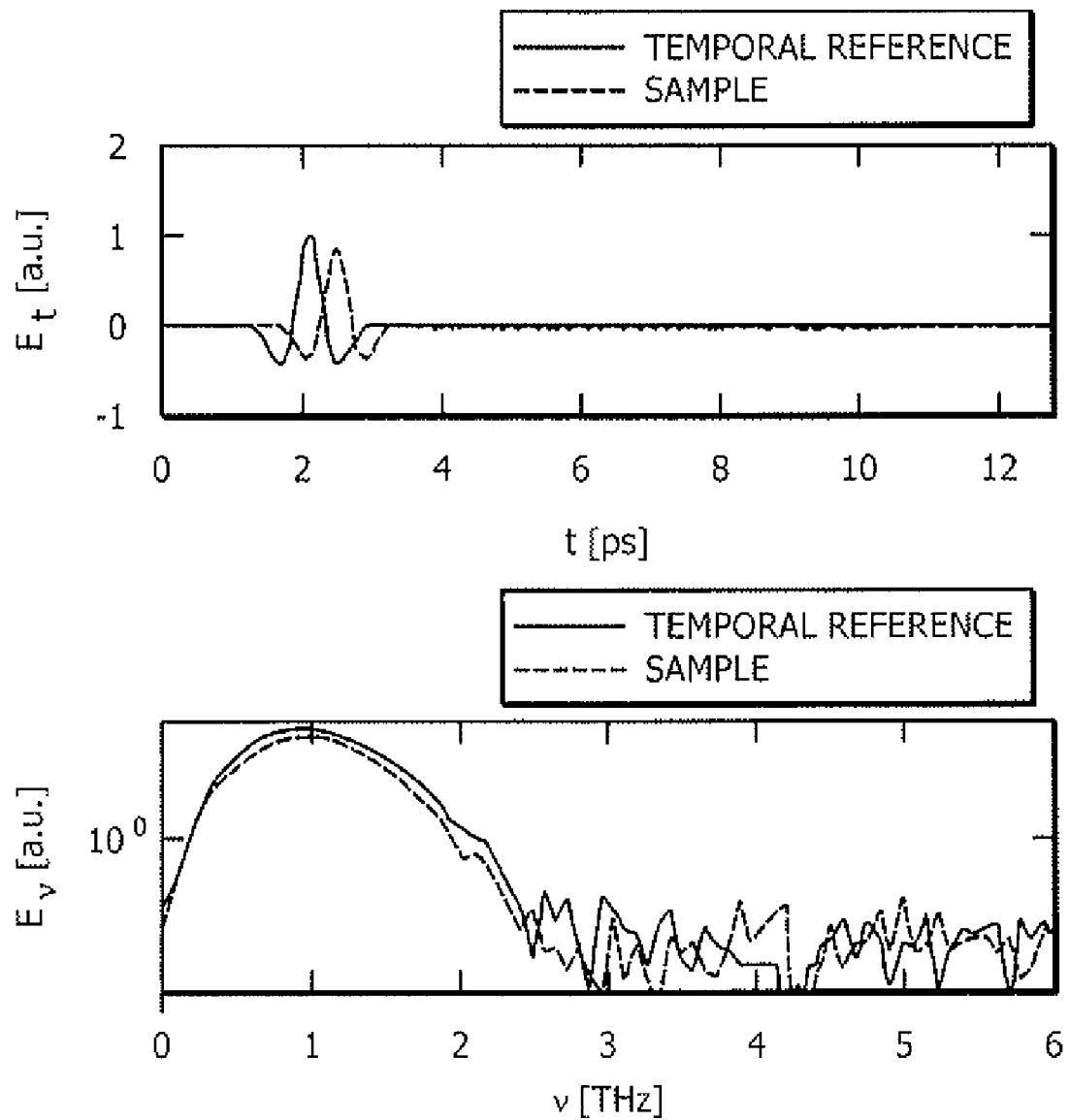
FIG. 5 shows typical input and output temporal pulses from a transmission-based THz or near THz-TDS system, according to an embodiment of the invention. The top traces show the temporal trace (time in picoseconds) for the electric field for the temporal reference and sample pulses obtained from the THz-TDS system and the bottom traces are their Fourier transforms.

Typical input and output temporal pulses from the THz-TDS are shown in FIG. 5. The top traces show the temporal trace (time in picoseconds) for the electric field for the temporal reference and sample pulses obtained from the THz-TDS system and the bottom traces are their Fourier transforms (frequency in THz).

Figure 6:
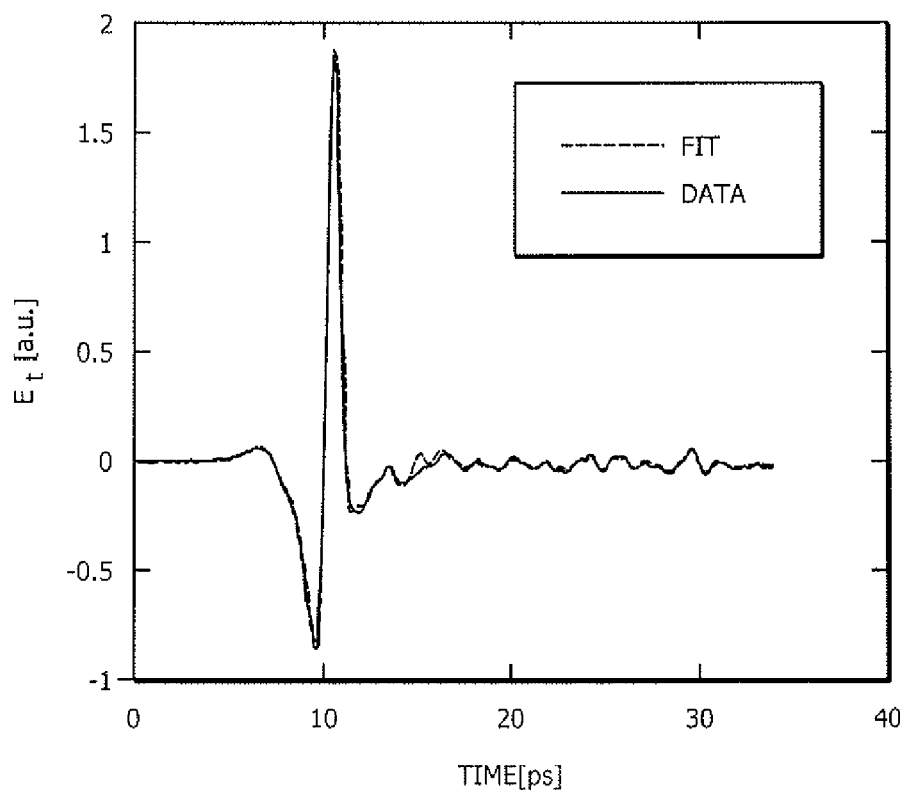
FIG. 6 shows a physical model fitted to the signal data obtained by transmission of a THz pulse through paper.

In step 208, in the case of a transmittance system, in order to obtain the physical thickness and dry weight volume fraction of the sheet material sample a transmittance function for the sheet material can be used (see equation (1) provided above). The parameters in the transmittance function can be adjusted to minimize the least squares error between the calculated transmission pulse and the measured transmitted pulse, thus fitting the physical model using a two parameter least squares fit. FIG. 6 shows a physical model fitted to the signal data obtained by transmission of a THz pulse through paper. The calculated transmission pulse can be found using the convolution (in time domain) of the reference pulse with the transmittance function.

Defining, $$y_o^{calc}[k] = IFFT(\{Y_i[\omega] \cdot T(\omega, h, v_f)\})$$

The error function can be defined as:

$$\text{Error} = \sum_k |y_o^{meas}[k] - y_o^{calc}[k]|^2 \quad (10)$$

$h$: Physical Thickness $v_f$: Dry weight volume fraction

Minimizing the error function above can provide the physical thickness (h) and dry weight volume fraction, $v_f$ of the paper or other sheet material. In step 209, the PM and then the BW can be calculated as follows:

$$PM = \frac{\rho_f}{\rho_w}\left(\frac{1}{v_f} - 1\right) \quad (11)$$

$$BW = \frac{WW}{PM} \quad (12)$$

Where, $\rho_f$: Fiber density
$\Sigma_w$: Water density

Figure 7:
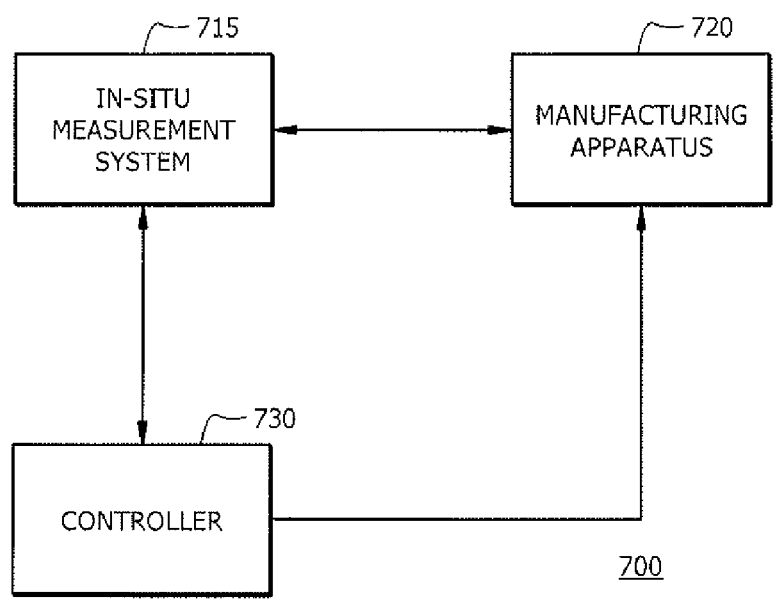
FIG. 7 is block diagram of an exemplary close loop controlled sheet material manufacturing system that provides in-situ measurements during the paper-making process. The system includes a process controller that uses the in-situ measurements for controlling process variables to maintain output quality and minimize the quantity of rejected product.

FIG. 7 is block diagram of and exemplary close loop controlled sheet material manufacturing system 700 that provides in-situ coincident measurements of a plurality of properties of a sheet material during the sheet material (e.g. paper) making process. The closed lop control provided as described below helps control process variables to maintain output quality and minimize the quantity of rejected product. The system 700 comprises a sheet material manufacturing apparatus 720 and a process controller 730 that uses the in-situ measurements from an in-situ measurement system 715. Measurement system 715 can be a reflection-based system, or a transmission based system such as system 100 shown in FIG. 1. Although shown as wire connected, communications between the components of system 700 can be wired, optical (e.g. fiber optic), or over the air (e.g. RF) or combinations thereof.

The controller 730 can process the electrical detection signals received and determine one or more paper quality properties, for example, the moisture profile achieved, and how the moisture profile should be updated during the papermaking process from "wet-end"-to-press and press-to-dryers at the "dry-end" in the case of a paper making system. As known in the art, the moisture profile can have significant impact on known variables in the paper making process such as sheet tension profiles, sheet breaks, shrinkage, winder efficiency, pressroom operation.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. for example, embodiments of the invention can include scanning measurements across the sheet material by scanning the transmitter and detectors in what is known as the cross direction (CD), or the measurements can be made at multiple locations down the length of the paper machine in what is known as the machine direction (MD).

Figures are also merely representational and may not be drawn to scale. Certain proportions thereof may be exaggerated, while others may be minimized. Accordingly, the specification and drawings are to be regarded in an illustrative rather than a restrictive sense.

Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description. Therefore, it is intended that the disclosure not be limited to the particular embodiment(s) disclosed as the best mode contemplated for carrying out this invention, but that the invention will include all embodiments falling within the scope of the appended claims.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims.

We claim:

1. An in-situ time domain spectroscopy (TDS)-based method for non-contact characterization of properties of a sheet material produced by a manufacturing system, comprising: providing a time domain spectrometry system and calibration data for said system, said calibration data comprising transmitted power or field through or reflected power or field from said sheet material as a function of a moisture content of said sheet material; directing at least one pulse of THz or near THz radiation having a frequency between 0.05 THz and 50 THz at a sample location on a sheet material sample while being processed by said manufacturing system; synchronously detecting transmitted or reflected radiation comprising at least one transmitted or reflected pulse from said sample location to obtain sample data, and processing said sample data together with said calibration data to determine at least one property of said sheet material sample selected from caliper, basis weight and moisture content; wherein said calibration data comprises a calibration curve, said calibration curve based on a ratio of a transmitted or reflected power or field for a non-interacted reference pulse sample having a path exclusive of said sheet material and a transmitted power or field through or reflected power or field from said sheet material.

2. The method of claim 1, wherein said method is an exclusively non-contact method, said sample data is coincident data, and said at least one property includes said caliper, said basis weight and said moisture content, said caliper, said basis weight and said moisture content all obtained from said coincident data.

3. The method of claim 1, further comprising the step of generating said calibration data, wherein said generating comprises measuring said transmitted or reflected power or field for a plurality of reference pulse samples of said sheet material, said plurality of reference pulse samples having different levels of said moisture content.

4. The method of claim 1, wherein said calibration curve comprises $$WW(y_i(t), y_o(t)) = m \times \log_e\left(\frac{PSD(y_i(t))}{PSD(y_o(t))}\right) + C$$

wherein WW is a water weight in grams per square meter (GSM), $y_i(t)$ is said non-interacted reference pulse sample, $y_o(t)$ is the output for said transmitted pulse and m and C are constants, and PSD is the integrated power spectral density.

5. The method of claim 3, wherein said calibration data further comprises a dry content density and a dry content refractive index for said sheet material.

6. The method of claim 1, wherein said caliper and a dry weight volume fraction of said sheet material are determined using a transmittance comprising function or a reflection comprising function comprising a plurality of parameters.

7. The method of claim 6, further comprising adjusting at least a portion of said plurality parameters of said transmittance or said reflectance comprising function for minimizing a least squares error between a calculated transmission or reflected pulse and said transmitted or said reflected pulse, wherein said minimizing provides said caliper and said dry weight volume fraction.

8. The method of claim 1, further comprising the step of calculating percent moisture and basis weight for said sheet material sample from a dry weight volume fraction, water weight and a density of constituent materials of said sheet material.

9. The method of claim 1, wherein said sheet material and said sheet material sample comprise paper.

10. An in-situ time domain spectroscopy (TDS)-based method for characterizing a plurality of properties of a sheet material while being produced by a manufacturing system, comprising: providing a time domain spectrometry system and calibration data for said system, said calibration data comprising transmitted power or field through or reflected power or field from said sheet material as a function of a moisture content of said sheet material; directing at least one pulse of THz or near THz radiation having a frequency between 0.05 THz and 50 THz at a sample location on a sheet material sample while being processed by said manufacturing system; synchronously detecting transmitted or reflected radiation comprising at least one transmitted or reflected pulse from said sample location to obtain sample data, wherein said sample data is coincident sample data, and processing said coincident sample data together with said calibration data to determine caliper, basis weight and moisture content of said sheet material; wherein said calibration data comprises a calibration curve, said calibration curve based on a ratio of a transmitted or reflected power or field for a non-interacted reference pulse sample having a path exclusive of said sheet material and a transmitted power or field through or reflected power or field from said sheet material.

* * * * *